United States Patent [19]

Gourvest et al.

[11] Patent Number: 5,081,114
[45] Date of Patent: Jan. 14, 1992

[54] STEROIDS

[75] Inventors: Jean-Francois Gourvest, Joinville Le Pont; Dominique Lesuisse, Paris, both of France

[73] Assignee: Roussel Uclaf, Paris, France

[21] Appl. No.: 633,288

[22] Filed: Dec. 24, 1990

[30] Foreign Application Priority Data

Dec. 22, 1989 [FR] France ............................... 89 17048

[51] Int. Cl.$^5$ ............................................. A61K 31/56
[52] U.S. Cl. .................................... 514/177; 552/530; 552/531; 552/632
[58] Field of Search ...................... 552/530, 531, 632; 514/177

[56] References Cited

U.S. PATENT DOCUMENTS 4,054,651 10/1977 Bensen et al. ........................ 552/632
4,150,127 4/1979 Anner et al. ........................ 552/632
4,309,423 1/1982 Biollaz .................................. 514/177

Primary Examiner—Richard L. Raymond
Assistant Examiner—Kimberly J. Kestler
Attorney, Agent, or Firm—Bierman and Muserlian

[57] ABSTRACT

A compound of the formula

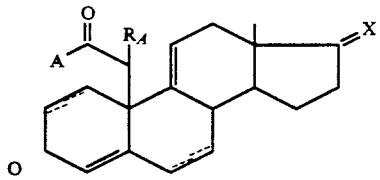

wherein R is selected from the group consisting of hydrogen,

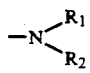

alkyl and alkoxy of 1 to 12 carbon atoms, aryl and aryloxy of 6 to 12 carbon atoms and aralkyl and aralkoxy of 7 to 12 carbon atoms, $R_1$ and $R_2$ are individually alkyl of 1 to 6 carbon atoms or taken together with the nitrogen atom to which they are attached form a 5 or 6 membered heterocycle optionally containing a second heteroatom of —S—, —O— or —N—, $R_A$ is selected from the group consisting of hydrogen, halogen, —OH, alkyl, alkylthio and alkoxy of 1 to 6 carbon atoms, —NH$_2$, mono- and dialkylamino of 1 to 6 alkyl carbon atoms, carbamoyl and alkoxy carbamoyl of up to 7 carbon atoms, X is —O— or

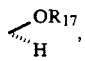

$R_{17}$ is selected from the group consisting of hydrogen, alkyl of 1 to 12 carbon atoms and acyl of an organic carboxylic acid of 1 to 12 carbon atoms and the dotted lines at 1(2) and 6(7) indicates an optional double bond, with the proviso that $R_A$ is not hydrogen when R is alkoxy, aryloxy or aralkoxy having aromatic specific activity useful in treating cancers.

9 Claims, No Drawings

STEROIDS

STATE OF THE ART

Related prior art includes U.S. Pat. Nos. 4,495,102 and 4,096,254.

The observation according to which approximately 35% of breast cancers are estrogen-dependent has led to research into ways of limiting the production of estrogens. After having using surgical methods consisting of suppressing the sources of estrogens (ovaries) or the sources of their biosynthetic precursors, the androgens (suprarenal glands), the development of less traumatizing methods has been sought. [ABUL-HAJJ., Steroid Biochem, Vol. 13 (1980), p. 1935; BRODIE, Cancer Res., Vol. 42, (1982), p. 3312].

In this respect, the specific inhibition of the last enzymatic stage of the aromatization of 3-keto-delta $^4$ androgens into phenolic estrogens appears to be the most effective and least disturbing method. The enzyme responsible for this conversion is a mono-oxygenase known as being a cytochrome P450: AROMATASE (BRODIE, J. Endocrinol. Invest., Vol. 2 (1979), p. 445) which requires oxygen and NADPH (Reduced form of Nicotinamide Adenine Dinucleotide Phosphate) to effect the aromatization of androgens into estrogens.

Based on another mechanism, other authors (for example, MARCOTTE et al, Biochemistry, Vol. 21, (1982), p. 2773, FLYNN et al, Biochem. Biophys. Res. Com., Vol. 103, (1981), p 713) have proposed suicide inhibitors for Aromatase. Competitive inhibitors such as Aminogluthetimide have also been proposed in the treatment of metastasic breast cancers. This product however has been shown as not being specific to Aromatase. In fact, it attacks enzymatic processes other than that which leads from androgens to estrogens.

OBJECTS OF THE INVENTION

It is an object of the invention to provide the novel steroids of formula I and a novel process for their preparation.

It is another object of the invention to provide novel compositions and a method of inducing aromatase specific activity in warm-blooded animals.

These and other objects and advantages of the invention will become obvious from the following detailed description.

THE INVENTION

The novel steroids of the invention have the formula

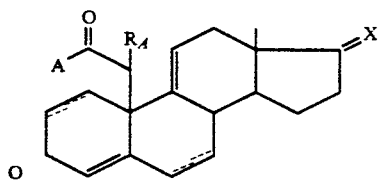

I wherein R is selected from the group consisting of hydrogen,

alkyl and alkoxy of 1 to 12 carbon atoms, aryl and aryloxy of 6 to 12 carbon atoms and aralkyl and aralkoxy of 7 to 12 carbon atoms, $R_1$ and $R_2$ are individually alkyl of 1 to 6 carbon atoms or taken together with the nitrogen atom to which they are attached form a 5 or 6 membered heterocycle optionally containing a second heteroatom of —S—, —O— or —N—, $R_4$ is selected from the group consisting of hydrogen, halogen, —OH, alkyl, alkylthio and alkoxy of 1 to 6 carbon atoms, —NH$_2$, mono- and dialkylamino of 1 to 6 alkyl carbon atoms, carbamoyl and alkoxy carbamoyl of up to 7 carbon atoms, X is —O— or

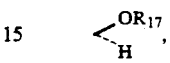

$R_{17}$ is selected from the group consisting of hydrogen, alkyl of 1 to 12 carbon atoms and acyl of an organic carboxylic acid of 1 to 12 carbon atoms and the dotted lines at 1(2) and 6(7) indicate an optional double bond, with the proviso that $R_4$ is not hydrogen when R is alkoxy, aryloxy or aralkoxy.

Examples of alkyl of 1 to 6 carbon atoms are methyl, ethyl, propyl, isopropyl, n-butyl, tert.-butyl, isobutyl, sec.-butyl, pentyl and hexyl. Alkyls of 1 to 12 carbon atoms include besides the foregoing alkyls, linear or branched heptyl, octyl, nonyl, decyl, undecyl and dodecyl. Examples of alkoxy are derived from the said alkyls with methoxy and ethoxy being preferred.

Examples of

includes amines individually alkyl of 1 to 6 carbon atoms but preferably dimethylamino or a heterocycle of 5 membered ring such as pyrrolidinyl or a 6 membered ring such as piperidinyl, moropholinyl or piperazinyl optionally substituted on the nitrogen with alkyl of 1 to 4 carbon atoms such as methyl or ethyl.

Examples of aryl radicals are carbocyclic aryl such as phenyl or naphthyl or heterocyclic aryls with 5 or 6 membered rings containing at least one heteroatoms chosen preferably from oxygen, sulfur and nitrogen. Examples of heterocyclic aryls with 5 links are furyl, thienyl, pyrrolyl, thiazolyl, oxazolyl, imidazolyl, thiadiazolyl, pyrazolyl and isoxazolyl. Examples of heterocyclic aryls with 6 links are pyridyl, pyrimidinyl, pyridazinyl and pyrazinyl. Among the condensed rings are indolyl, benzofurannyl, benzothienyl and quinolinyl. Phenyl is preferred. The aryloxys are derived from the aryls mentioned above with phenoxy being preferred.

Examples of aralkyl are benzyl and phenethyl preferably and the aralkoxys are benzyloxy and phenethoxy preferably.

R is preferably hydrogen, methyl, ethoxy and dimethylamino and the alkyl of $R_{17}$ can be chosen from the values indicated above. The alkyl of 1 to 6 carbon atoms and especially methyl are preferred.

Among the acyl of $R_{17}$ are acyls of carboxylic acids such as acetyl, propionyl or benzoyl. Among the halogen atoms, chlorine, fluorine or bromine can be cited.

Among the alkylthios are radicals corresponding to the above-mentioned alkyl such as methylthio or ethylthio.

Among the alkoxycarbonyl are those derived from alkyls mentioned above and methoxycarbonyl and especially ethoxycarbonyl are preferred.

A preferred group of compounds are those of the formula

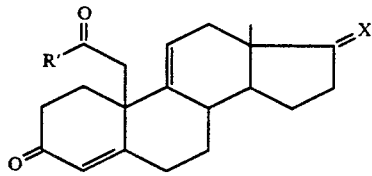  I' wherein R' is hydrogen, —N(R'$_1$)$_2$ in which R'$_1$ is alkyl of 1 to 4 carbon atoms or R' is alkyl or alkoxy of 1 to 4 carbon atoms, X is oxygen or

A preferred compound is $^{4,9(11)}$-androstadiene-3,17-dione-19-carboxaldehyde.

The process for the preparation of the compounds of formula I comprises reacting a compound of the formula

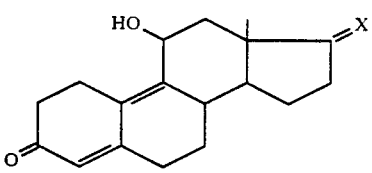  IL wherein X has the above definition with either a product of the formula

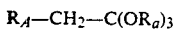  III in which R$_A$ has the above meaning, R$_a$ is alkyl or arylalkyl of at most 12 carbon atoms to obtain the products of formula Ia corresponding to the products of formula I in which R is alkoxy, aryloxy or aralkoxy of at most 12 carbon atoms, R$_A$ has the above meaning and the dotted lines in positions 1(2) and 6(7) do not represent a second bond between the carbons that carry them, or a product of the formula

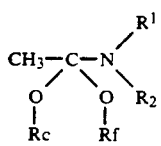  IV in which R$_1$ and R$_2$ have the above meaning, Re and Rf are individually alkyl of 1 to 4 carbon atoms to obtain the products of formula Ib corresponding to the products of formula I in which R is

in which R$_1$ and R$_2$ have the above meaning, R$_A$ is hydrogen and the dotted lines in position 1(2) and 6(7) do not represent a second bond between the carbons that carry them or a product of the formula

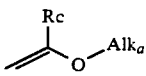  V in which Rc is hydrogen or alkyl or aryl of at most 12 carbon atoms and Alk$_a$ is alkyl of 1 to 4 carbon atoms to obtain the products of formula Ic corresponding to the products of formula I in which R is hydrogen or alkyl or aryl of at most 12 carbon atoms, R$_A$ is hydrogen and the dotted lines in positions 1(2) and 6(7) do not represent a second bond between the carbons that carry them and the products of formulae Ia, Ib or Ic which if desired are subjected to at least one of the following reactions introduction of a double bond in position 1(2)
introduction of a double bond in position 6(7)
reduction of the 17-ketone when X is oxygen,
etherification or esterification of the products in which X is

In a preferred method of the process, the action of the product of formula III on the products of formula II is carried out in the presence of an acid such as an organic acid like acetic acid, propionic acid or p-toluenesulfonic acid in a solvent of high boiling point such as toluene or xylene. The action of the product of formula IV is also carried out in a high boiling point solvent such as toluene or xylene as mentioned above. In formula IV, Re and Rf each are preferably ethyl or methyl or together form ethylene and the reaction of the product of formula V is preferably carried out in the presence of mercury acetate at a high temperature.

The reaction of the products of formula III, IV and V with a product of formula II gives rise to what is conventionally called a Claisen rearrangement. The optional introduction of a double bond in position 1(2) is effected effected using DDQ preferably in a solvent such as dioxane and the optional introduction of a double bond in position 6(7) is effected using an orthoformate such as ethyl orthoformate in the presence of p-toluene sulfonic acid or camphorsulfonic acid in a common solvent such as ethanol, the reaction being followed by that of chloranile in a solvent such as aqueous acetone or aqueous tetrahydrofuran. The optional reduction of the 17-ketone is effected using a hydride such as sodium borohydride in a solvent such as methanol and the optional etherification of the 17-alcohol is effected first by the action of a strong base such as potassium tert-butylate or potassium hydride followed by the action of a halide or of a pseudo-halide derivative of R$_{17}$ of the formula R$_{17}$-X in which X is preferably chlorine or bromine or mesyl or tosyl with the reaction undertaken preferably in a polar solvent. The optional esterification of the 17$\beta$-alcohol is undertaken preferably using a reactive derivative of an acyl such as an acid halide, preferably the acid chloride or a mixed or symmetrical anhydride. The operation can also be carried out with the carboxylic acid corresponding to the acyl radical if it is desired to introduce it by using a dehydration agent such as dicyclohexylcarbodiimide (DCC).

The compositions of the invention having aromatase specific activity (cytochrome P450 aromatase) comprises an effective amount of at least one compound of formula I and an inert pharmaceutical carrier or excipient. The compositions may be in the form of tablets, dragees, capsules, granules, suppositories, pessaries, ointments, creams, gels, patches and injectable preparations.

Examples of suitable excipients are talc, arabic gum, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions due to their aromatase specific activity (cytochrome P450 aromatase) are useful for the treatment of cancers of the breast, endometrium, ovary and pancreas, gynecomastia, benign breast disorders, endometriosis, polycystic affections of the ovary and prostatic hyperplasia and more generally in the treatment of hyperestrogenemia.

The novel method of inducing aromatase specific activity in warm-blooded animals, including humans, comprises administering to warm-blooded animals an amount of a compound of formula I sufficient to induce aromatase specific activity. The compounds may be administered orally, rectally, topically or parenterally and the usual daily dose is 0.0066 to 0.133 mg/kg depending on the condition treated, the specific compound and the method of administration.

The starting materials of formula II are described in U.S. Pat. Nos. 3,211,764 and 3,282,785. The compounds of formula III can be prepared by known methods such as described in J. Gen. Chem., Vol. 6, p. 576 to 583 (1936), Chem. Abst., Vol. 30, p. 5583 (1936), Chem. Abst., Vol. 41, p. 5904a (1947), Wh. Graham. Tet. Lett., Vol. 27, p. 2223 (1969) or JACS. Vol. 64, p. 1825.7 (1942). Generally, the products of formula III are prepared starting with $R_4$—$CH_2$—$C\equiv N$ type products.

In the following examples there are described several preferred embodiments to illustrate the invention. However, it should be understood that the invention is not intended to be limited to the specific embodiments.

EXAMPLE 1

Ethyl $4,9(11)$-androstadiene-3,17-dione-19-carboxylate

A mixture of 500 mg of $4,9$-androstadiene-11-ol-3,17-dione (described in U.S. Pat. No. 3,282,785), 5 ml of triethyl orthoacetate and 6.4 mg of propionic acid was heated to 137° C. After 4 hours of heating, the reaction mixture was concentrated to dryness and the crude mixture was chromatographed on silica. (Eluant a mixture of ethyl acetate-hexane 1/1) to obtain 503 mg of the expected product with a Rf=0.33.

NMR ($CDCl_3$, 250 MHz): 0.94 (s, 18-Me), 1.23 (t, $COOCH_2CH_3$), 3.94 to 4.29 (m, $COOCH_2CH_3$), 5.61 (m, H11), 5.84 (wide s, H14).

IR ($CHCl_3$): 1732 cm$^{-1}$ (17-ketone) 1662 cm$^{-1}$, 1612 cm$^{-1}$ (conjugated ketone).

EXAMPLE 2

N,N-dimethyl-$4,9(11)$-androstadiene-3,17-dione-19-carboxamide

A mixture of 500 mg of $4,9$-androstadiene-11-ol-3,17-dione, 350 mg of dimethylacetal dimethylacetamide and 30 ml of toluene was refluxed for 2 hours. The solvent was evaporated off under reduced pressure and the crude product was crystallized from isopropyl ether to obtain 495 mg of the expected product which was purified by crystallization from ethyl acetate.

NMR ($CDCl_3$, 300 MHz): 0.89 (s, 18-Me), 2.72 (m, 19-$CH_2$), 2.90 and 3.06 ($CONMe_2$), 5.71 (H11), 5.87 (H4).

IR ($CHCl_3$): 1735 cm$^{-1}$ (17-ketone), 1665 cm$^{-1}$ (conjugated ketone), 1643 cm$^{-1}$ (tertiary amide).

Analysis: $C_{22}H_{29}O_3N$; molecular weight=355.46; Calculated: %C 74.33, %H 8.22, %N 3.94; Found: 74.1, 8.1, 3.7

EXAMPLE 3

$4,9(11)$-androstadiene-3,17-dione-19-carboxaldehyde

A mixture of 4.5 g of $4,9$-androstadiene-11-ol-3,17-dione, 1.25 g of mercury acetate and 18 ml of ethyl vinyl ether was heated to 80° C. for 12 hours and then was poured into a 1/1 mixture of dichloromethane and ammonium chloride. The aqueous phase was extracted with dichloromethane and the organic extracts were dried over magnesium sulfate and concentrated to obtain 6.06 g of crude product. A precipitation in ether provided 3.79 g of the desired aldehyde which was crystallized from ethanol and dried at 150° C. under reduced pressure in the presence of phosphorous pentoxide.

NMR ($CDCl_3$, 250 MHz): 0.85 (s, 18-Me), 5.70 (H11), 5.87 (H4) 9.66 (t, CHO).

IR ($CHCl_3$): 1736 and 1406 cm$^{-1}$ (17-ketone), 1721 and 2740 cm$^{-1}$ (CHO), 1671 and 1615 cm$^{-1}$ (conjugated ketone); 1632 cm$^{-1}$ (C=C).

Analysis $C_{20}H_{24}O_3$; molecular weight=312.39; Calculated: %C 76.89, %H 7.74; Found: 76.7, 8.0

EXAMPLE 4

10-(2-oxopropyl)-$4,9(11)$-estradiene-3,17-dione

A mixture of 3 g of $4,9$-androstadiene-11-ol-3,17-dione, 834 mg of mercury acetate and 12 ml of methyl isopropenyl ether was heated to 80° C. for 12 hours and then was poured into a mixture of dichloromethane and ammonium chloride. The aqueous phase was extracted with dichloromethane and the combined organic extracts were dried and concentrated. The crude mixture was chromatographed on silica (eluant:ethyl acetate/hexane 1:1) to obtain 390 mg of the expected product with a Rf=0.21 which is crystallized from an ether/ethanol mixture.

NMR ($CDCl_3$), 250 MHz): 0.91 (s, 18 Me), 2.16 (s, $COCl_3$) 2.76 and 2.88 (2d, J=15, $CH_2CO$), 5.66 (m, H11) 5.83 (s, H4).

IR ($CHCl_3$: 1717 and 1705 cm$^{-1}$ ($COCH_3$), 1735 cm$^{-1}$ (17-keto) 1669 and 1615 cm$^{-1}$ (3 keto).

Analysis: $C_{21}H_{26}O_3$; molecular weight=326.42; Calculated: %C 77.27, %H 8.03; Found: 71.10, 8.0

EXAMPLE 5

N,N-dimethyl-$4,9(11)$-androstadiene-17-ol-3-one-19-carboxamide

A mixture of 1 g of $4,9$-androstadiene-11,17-diol-3-one, 1.158 g of dimethylacetal of dimethylacetamide and 50 ml of toluene was refluxed for 3 hours. After concentration under reduced pressure and chromatography on silica (eluant:ethyl acetate-methanol 9-1), 930 mg of the expected product were obtained.

IR ($CHCl_3$): 1642 cm$^{-1}$ tertiary amide) 1662, 880 and 869 cm$^{-1}$ (conjugated ketone).

SM: 357 (M$^+$).

EXAMPLE 6

Ethyl $^{4,9(11)}$-androstadien-3,17-dione-19-dicarboxylate 300 mg of $^{4,9}$-androstadien-11-ol-3,17-dione, 2 ml of triethyl orthomalonate and 10 μl of propionic acid were heated to 140° C. for 3 hours. A few drops of triethylamine were added, followed by con-centrating to dryness under reduced pressure. The residue was chromatographed on silica (eluant:ethyl acetate-cyclohexane 0-1 then 3-7) to obtain 360 mg of expected product with a Rf=0.54 (cyclohexane-ethyl acetate 1-1).

IR (CHCl$_3$): 1750 cm$^{-1}$ (esters); 1734 cm$^{-1}$ (17-keto); 1669 cm$^{-1}$ (conjugated ketone): 1636 and 1620 cm$^{-1}$ (C=C).

NMR (CDCl$_3$, 300 MHz): 0.87 (s, 18 Me); 1.22 (m, COOEt); 4.15 (m, COOEt); 4.26 (s, CH(COOEt)$_2$; 5.74 (m, H11); 5.91 (s, H4).

EXAMPLE 7

Ethyl $^{4,9(11)}$-androstadien-3,17-dione-19-chloro-19-carboxylate 300 mg of $^{4,9}$-androstadien-11-ol-3,17-dione, 3 ml of triethyl orthochloroacetate [prepared as in JACS, Vol. 64, p 1825 to 1827, (1942)] and 10 l of propionic acid were heated for 2 hours at 140° C. After partial concentration under reduced pressure, the precipitate formed was eliminated by filtration and the filtrate was chromatographed on silica (eluant:ethyl acetate-cyclohexane 3-7) to obtain 177 mg of the expected product.

IR (CHCl$_3$): 1739 cm$^{-1}$(17-keto); 1672 cm$^{-1}$ (conjugated ketone); 1636 and 1616 cm$^{-1}$ (C=C).

NMR (CDCl$_3$, 300 MHz): 5-1 mixture of 2 diastereisomers: 0.93 and 0.94 (18 Me); 1.24 and 1.28 (2t, COOEt); 4.50 and 4.30 (COOEt); 4.89 and 4.99 (2s, CH(Cl)COOEt); 5.78 (m, H11); 5.92 and 6.01 (H4).

PHARMACOLOGICAL STUDY

Inhibition dependent on the concentration (measurement of the CI$_{50}$=concentration of the inhibitor necessary to reduce the enzymatic activity by 50%).

Human placentas were used which were washed one hour at most after delivery, then perfused with physiological serum (5 liters) via the umbilical vein, then deep-frozen at $-40°$ C.

1) Obtaining the placental microsomes

The placentas were thawed out at 4° C., then homogenized (1:3) in a 10 mM phosphate buffer, pH=7.0 containing 100 milimoles of potassium chloride (KCl), 10 millimoles of dithiothreitol (DTT), potassium chloride (KCl), 10 millimoles of dithiothreitol (DTT), 10 millimoles of ethylenediaminetetra-acetic acid (EDTA), 40 millimoles of nicotinamide and 250 millimoles of sucrose. The homogenates were then subjected to different phases of centrifugation until a "9000 g" supernatant was obtained (corresponding to cytosol and to endosplasmic reticulum). This supernatant was subjected to an ultracentrifugation stage for 90 minutes at 105,000 g to obtain the microsomal deposit. The microsomes were suspended in a 50 millimoles phosphate buffer, pH=7.4, containing 100 millimoles of KCl, 1 millimole of EDTA, 1 millimole of DTT and glycerol (10%). The microsomal suspension was aliquoted and the fractions were deep-frozen at the temperature of liquid nitrogen. The protein concentration of the microsomal suspension was determined by the BRADFORD method [BRADFORD, Anal. Biochem., Voml. 72, 1976) p. 248].

2. Measurement of the CI$_{50}$ of each inhibitor

To 960 microliters of phosphate buffer (50 millimoles, pH=7.2), 2.5 millimoles glucose-6-phosphate, and containing 0.16 international units of glucose-6-phosphate deshydrogenase (G-6PDH), the following were added in this order:

1°-10 microliters of inhibitor solubilized in dimethyl sulfoxide (DMSO) to give final concentrations from $10^{-6}$M to $10^{-9}$M.

2°-10 microliters of substrate which was 60 nM Androstenedione solubilized in ethanol and containing 1β-2β-(H$^3$)-Androstenedione at a known isotopic dilution of approx. 200,000 disintegrations per minute.

3°-10 microliters of microsomal suspension equivalent to 25 microgramms of proteins per test.

Then the enzymatic reaction was very rapidly initiated by the addition of 10 microliters of reduced nicotinamide adenine dinucleotide phosphate (NADPH) solubilized in water. After stirring, each test was incubated at 37° C. for 10 minutes. The reaction was then stopped by the addition of 4 ml of chloroform. After vigorous stirring of the tubes, they were decanted and centrifuged at 4° C. for 10 minutes at a speed of 3,000 revolutions per minute or 600×g. After centrifugation, and for each tube, 100 microliters of supernatant was removed and counted in the presence of a scintillating liquid. This method is derived from procedures described by REED et al in J. Biol. Chem., Vol. 251, (1976), p. 1625 and THOMPSON et al, J. Biol. Chem., Vol. 249, (1974), p. 5364.

The enzymatic activity (aromatase) was proportional to the percentage of tritium salted out in the form of tritiated water (H$^3_2$O) in the course of the reaction. The inhibition obtained for each concentration of each inhibitor product of the invention was calculated as a percentage of the controls (arbitrary 100%, obtained in the absence of any inhibitor). The CI$_{50}$ was equal to the concentration of inhibitor necessary to decrease the enzymaticactivity by 50% and the values of CI$_{50}$ obtained for inhibitor products of the product of Example 3: CI$_{50}$=8.5.10$^{-8}$M.

Various modifications of the products and method of the invention may be made without departing from the spirit or scope thereof and it is to be understood that the invention is intended to be limited only as defined in the appended claims.

What we claim is:

1. A compound of the formula

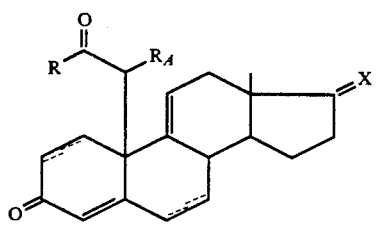

(I)

wherein R is selected from the group consisting of hydrogen, $$-N\begin{array}{c}R_1\\R_2\end{array}$$

alkyl and alkoxy of 1 to 12 carbon atoms, aryl and aryloxy of 6 to 12 carbon atoms and aralkyl and aralkoxy of 7 to 12 carbon atoms, $R_1$ and $R_2$ are individually alkyl of 1 to 6 carbon atoms or taken together with the nitrogen atom to which they are attached form a 5 or 6 membered heterocycle optionally containing a second heteroatom of —S—, —O— or —N—, $R_4$ is selected from the group consisting of hydrogen, halogen, —OH, alkyl, alkylthio and alkoxy of 1 to 6 carbon atoms, —NH$_2$, mono- and dialkylamino of 1 to 6 alkyl carbon atoms, carbamoyl and alkoxy carbamoyl of up to 7 carbon atoms, X is oxygen or $$\begin{array}{c}OR_{17}\\H\end{array}$$

$R_{17}$ is selected from the group consisting of hydrogen, alkyl of 1 to 12 carbon atoms and acyl of an organic carboxylic acid of 1 to 12 carbon atoms and the dotted lines at 1(2) and 6(7) indicate an optional double bond, with the proviso that $R_4$ is not hydrogen when R is alkoxy, aryloxy or aralkoxy.

2. A compound of claim 1 having the formula (I')

wherein R' is hydrogen or $$-N\begin{array}{c}R_1'\\R_1'\end{array}$$

or alkyl or alkoxy of 1 to 4 carbon atoms, $R'_1$ is alkyl of 1 to 4 carbon atoms and X is oxygen or $$\begin{array}{c}OH\\H\end{array}$$

3. A compound of claim 1 which is $^{4,9(11)}$-androstadiene 3,17-dione-19-carboxaldehyde.

4. A composition of aromatase specific activity (cytochrome P 450 aromatase) comprising an effective aromatase specific amount of at least one compound of claim 1 and an inert pharmaceutical carrier.

5. A composition of claim 4 having the formula (I')

wherein R' is hydrogen or $$-N\begin{array}{c}R_1'\\R_1'\end{array}$$

or alkyl or alkoxy of 1 to 4 carbon atoms, $R'_1$ is alkyl of 1 to 4 carbon atoms and X is oxygen or $$\begin{array}{c}OH\\H\end{array}$$

6. A composition of claim 4 wherein the active compound is $^{4,9(11)}$-androstadiene-3,17-dione-19-carboxaldehyde.

7. A method of inducing aromatase specific activity (cytochrome P 450 aromatase) in warm-blooded animals comprising administering to warm-blooded animals an effective amount of a compound of claim 1 sufficient to induce aromatase specific activity.

8. A method of claim 7 having the formula (I')

wherein R' is hydrogen or $$-N\begin{array}{c}R_1'\\R_1'\end{array}$$

or alkyl or alkoxy of 1 to 4 carbon atoms, $R'_1$ is alkyl of 1 to 4 carbon atoms and X is oxygen or $$\begin{array}{c}OH\\H\end{array}$$

9. A method of claim 7 wherein the active compound is $^{4,9(11)}$-3,17-dione-19-carboxaldehyde.

* * * * *